(12) United States Patent
Hochmair et al.

(10) Patent No.: US 8,340,774 B2
(45) Date of Patent: Dec. 25, 2012

(54) IMPLANTABLE DEVICE WITH REMOVABLE MAGNET

(75) Inventors: Erwin S. Hochmair, Axams (AT); Martin Zimmerling, Patsch (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1328 days.

(21) Appl. No.: 12/044,217

(22) Filed: Mar. 7, 2008

(65) Prior Publication Data

US 2008/0221641 A1    Sep. 11, 2008

Related U.S. Application Data

(60) Provisional application No. 60/893,455, filed on Mar. 7, 2007.

(51) Int. Cl.
*A61N 1/00* (2006.01)

(52) U.S. Cl. .......................................... 607/57; 607/60

(58) Field of Classification Search ............. 607/55–57, 607/60; 324/303; 343/788
See application file for complete search history.

(56) References Cited

U.S. PATENT DOCUMENTS

| | | | |
|---|---|---|---|
| 6,348,070 B1 * | 2/2002 | Teissl et al. | 623/11.11 |
| 6,517,476 B1 | 2/2003 | Bedoya et al. | |
| 2004/0012470 A1 | 1/2004 | Zimmerling et al. | 335/207 |
| 2005/0001703 A1 | 1/2005 | Zimmerling | 335/220 |
| 2005/0004629 A1* | 1/2005 | Gibson et al. | 607/60 |
| 2005/0256561 A1 | 11/2005 | Gantz et al. | 607/137 |

OTHER PUBLICATIONS

International Search Report and Written Opinion dated Jul. 16, 2008, PCT/US2008/056152.

* cited by examiner

*Primary Examiner* — Mark W Bockelman
(74) *Attorney, Agent, or Firm* — Sunstein Kann Murphy & Timbers LLP (57) ABSTRACT

An implantable device includes a receiving coil assembly including a magnet holding structure for containing an internal holding magnet which is reorientable in responsive alignment to an external magnetic field. The magnet holding structure is adapted for allowing removal and subsequent reinsertion of the internal holding magnet.

9 Claims, 7 Drawing Sheets

IMPLANTABLE DEVICE WITH REMOVABLE MAGNET

This application claims priority from U.S. Provisional Patent Application 60/893,455, filed Mar. 7, 2007, the contents of which are hereby incorporated by reference.

TECHNICAL FIELD

The present invention generally relates to an implantable device having a removable magnet. For example, this magnet may be located at the center of an implanted receiving coil for holding in place an external transmitter coil.

BACKGROUND ART

Figure 1:
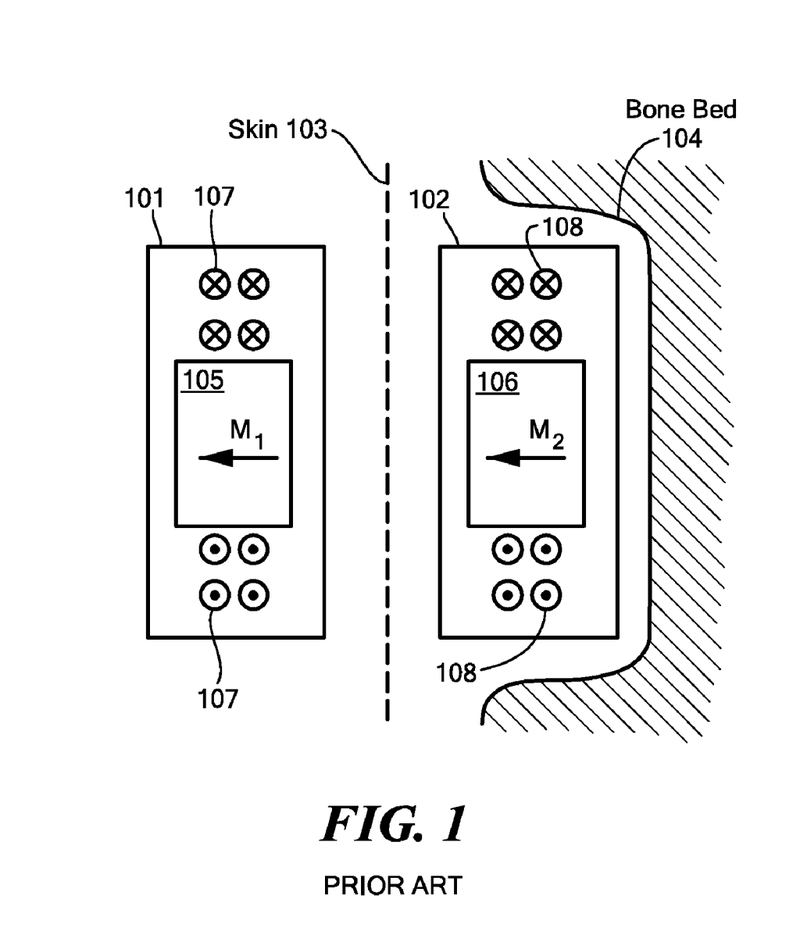
FIG. 1 shows a portion of a typical idealized cochlear implant according to the prior art.

Some implantable medical devices use magnets to hold internal and external pieces in proper position. For example, as shown in FIG. 1, an idealized cochlear implant system may include a receiving coil 108 located under the skin 103 and embedded in or just on top of the bone 104. A receiver magnet 106 is contained in the center of the receiving coil 108. An external transmitter housing 101 includes a transmitter magnet 105 that is positioned over the receiver magnet 106 so that the external transmitter housing 101 is held in place in an optimum position adjacent to the receiving coil assembly 102. When such an optimal position is maintained, an external transmitting coil 107 within the transmitter housing 101 can use inductive coupling to transmit a transcutaneous data and/or power signal to the receiving coil 108.

The receiving coil 108 may, for example, be encapsulated within some tissue-compatible organic material such as silicone or epoxy, forming a receiving coil assembly 102. In such an arrangement, the receiver coil assembly 102 is connected to receiver electronic circuits within a metal or ceramic case which is hermetically sealed from the surrounding tissue. Or, in another approach, the receiver magnet 106, receiving coil 108 and the receiver electronic circuits are all contained within a common hermetic case. In any such arrangement, the receiver magnet 106 is a permanently integrated part of the implant structure.

Figure 2:
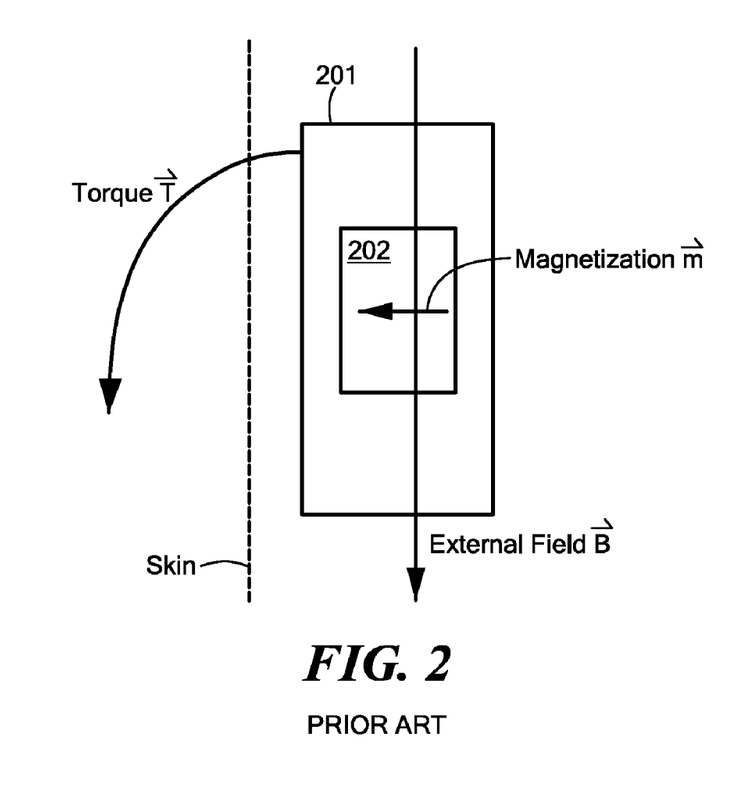
FIG. 2 shows effects of an external magnetic field on an implanted portion of a prior art device.

One problem arises when the patient undergoes Magnetic Resonance Imaging (MRI) examination. Interactions occur between the receiver magnet and the applied external magnetic field for the MRI. As shown in FIG. 2, the external magnetic field $\vec{B}$ from the MRI may create a torque $\vec{T}$ on an implanted receiver magnet 202, which may displace the receiver magnet 202 or the whole coil assembly 201 out of proper position. Among other things, this may damage the adjacent tissue in the patient. In addition, the external magnetic field $\vec{B}$ from the MRI may reduce or remove the magnetization $\vec{m}$ of the receiver magnet 202. As a result, the demagnetized receiver magnet 202 may no longer be strong enough after exposure to the external magnetic field $\vec{B}$ of the MRI to hold the external transmitter housing in proper position. The implanted receiver magnet 202 may also cause imaging artifacts in the MRI image, there may be induced voltages in the receiving coil, and hearing artifacts due to the interaction of the external magnetic field $\vec{B}$ of the MRI with the implanted device.

Figure 3:
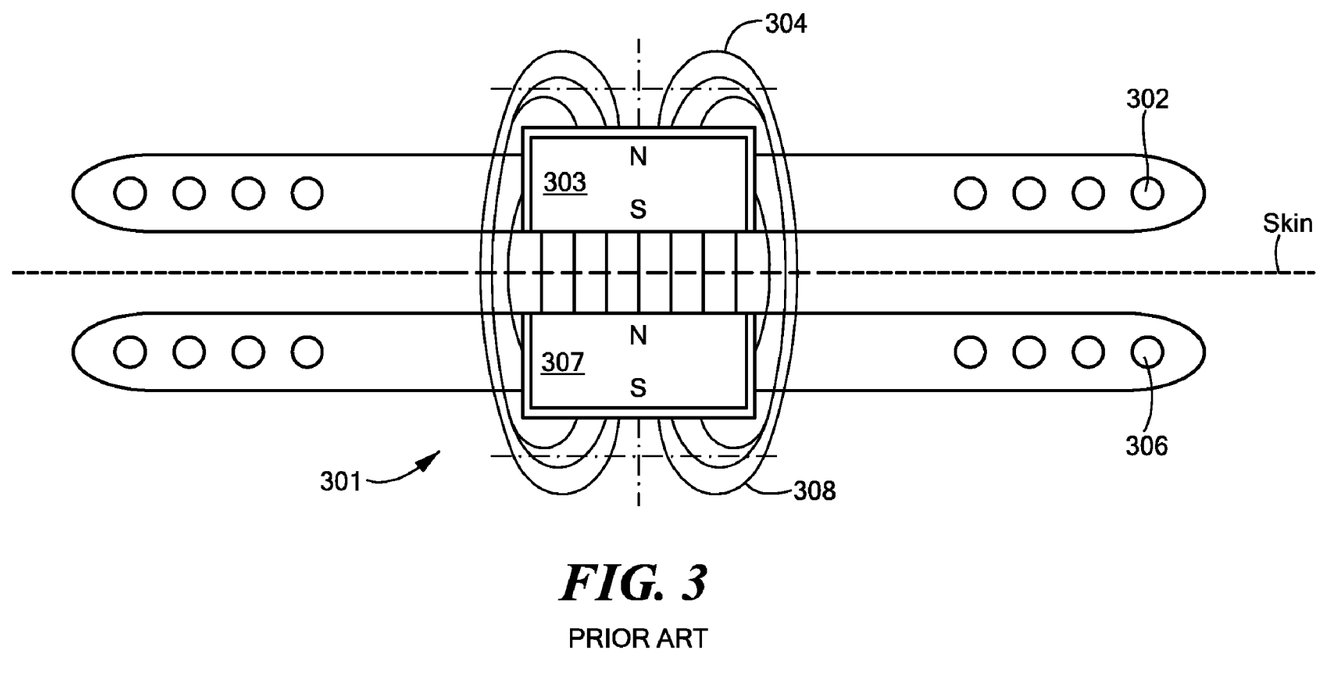
FIG. 3 shows a portion of a typical implant system using magnets according to the prior art.

Therefore, implants with removable magnets have been developed. FIG. 3 shows a portion of a typical implant system using magnets according to one approach used in the prior art. An external transmitter housing 301 includes transmitting coils 302 and an external holding magnet 303. The external holding magnet 303 has a conventional coin-shape and north and south magnetic poles as shown which produce external magnetic field lines 304. Implanted under the patient's skin is a corresponding receiver assembly 305 having similar receiving coils 306 and an internal holding magnet 307. The internal holding magnet 307 also has a coin-shape and north and south magnetic poles as shown which produce internal magnetic field lines 308. The internal receiver housing 305 is surgically implanted and fixed in place within the patient's body. The external transmitter housing 301 is placed in proper position over the skin covering the internal receiver assembly 305 and held in place by interaction between the internal magnetic field lines 308 and the external magnetic field lines 304. Rf signals from the transmitter coils 302 couple data and/or power to the receiving coil 306 which is in communication with an implanted processor module (not shown).

The arrangement in FIG. 3 differs from the earlier prior art in that the implant is designed so that the internal holding magnet 307 is removable by a first pre-MRI surgery. This eliminates the problems of torque, demagnetization, and image artifacts caused by the magnet during the MRI procedure. Then, after the MRI, a second post-MRI surgery is necessary to replace the internal holding magnetic 307. While this arrangement allows implant users to receive MRI's when necessary, the requirement for two surgeries raises issues and problems of its own.

Figure 4:
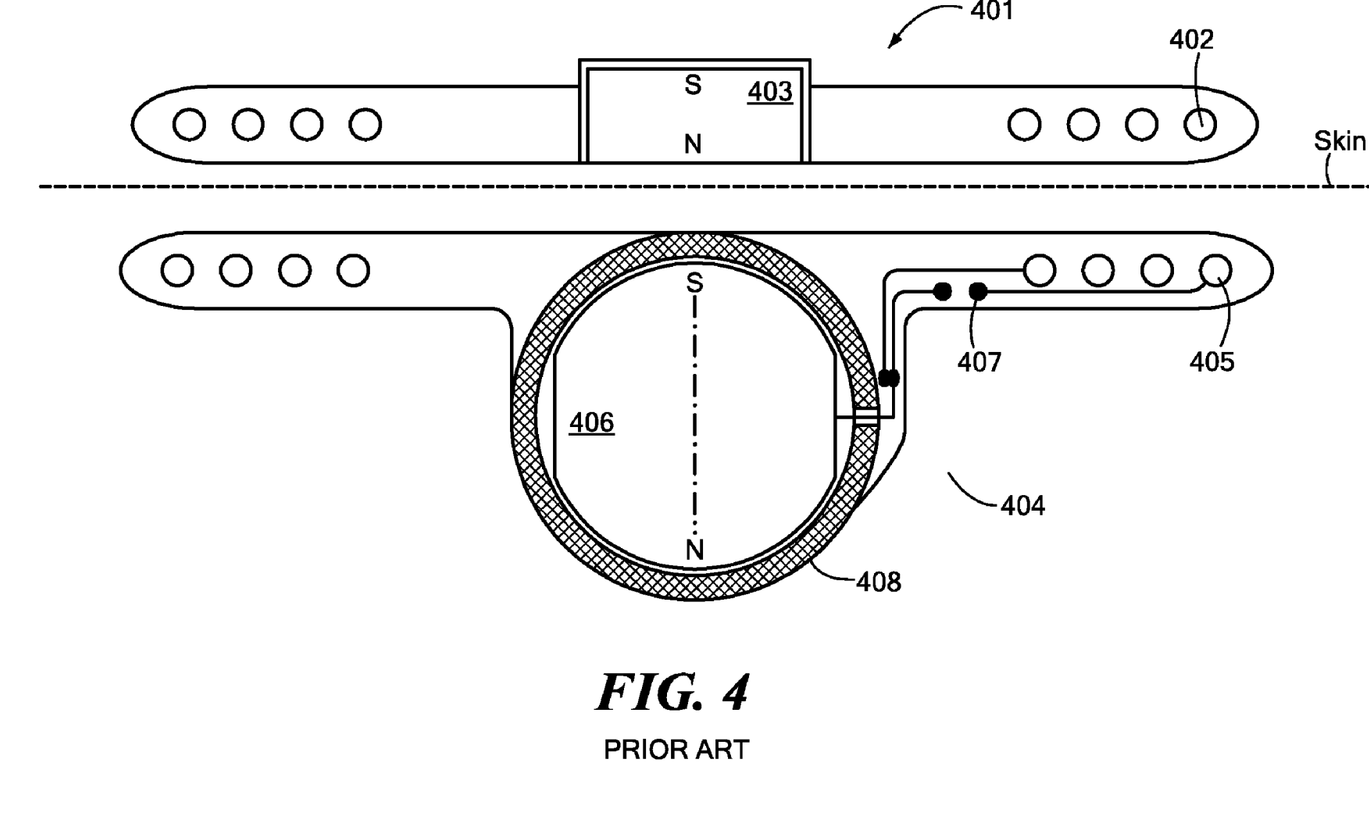
FIG. 4 shows a portion of a typical implant system using a low-torque magnet according to the prior art.

More recently, some MRI related problems have been addressed by using an implanted magnet structured to avoid producing torque in an MRI field. One example of such an arrangement is shown in FIG. 4, which is based on the disclosure of U.S. Patent Publication 20060244560, the contents of which are incorporated herein by reference. The external transmitter housing 401 is basically the same as in FIG. 3, with transmitting coils 402 and an external holding magnet 403. The implanted receiver assembly 404 has corresponding receiving coils 405 and an internal holding magnet 406, as well as connecting wiring 407 to a separate processor module. But in FIG. 4, the internal holding magnet 406 has a cylindrical or spherical shape. A ball-shaped welded case 408 (e.g., of titanium or niobium) hermetically encapsulates and isolates the internal holding magnet 406 from the body tissues (otherwise, it might rapidly corrode).

As a result, the internal holding magnet 406 is able to rotate to re-align itself to an external MRI magnetic field without producing a torque, becoming demagnetized, or creating induced voltages, etc. This avoids many of the problems of their earlier arrangement shown in FIG. 3. Typically, a patient having an implant as shown in FIG. 4 may undergo MRI without surgeries to remove and replace the internal holding magnet 406. But even in this arrangement, there may still be imaging artifacts due to the internal holding magnet 406, especially in the nearby region adjacent to the magnet.

SUMMARY OF THE INVENTION

Embodiments of the present invention are directed to an implantable device having a receiver coil assembly including a magnet holding structure for containing at least one internal holding magnet. The internal holding magnet is reorientable in responsive alignment to a direction of an external magnetic field. The magnet holding structure is adapted for allowing removal and subsequent reinsertion the at least one magnet with respect to the receiver coil assembly.

In specific embodiments, the at least one internal holding magnet may be spherical, and in some embodiments, there may be multiple spherical magnets. Or the internal holding magnet may be cylindrical, and some embodiments may have multiple cylindrical magnets. The magnet holding structure may use a resilient material to be temporarily deformable, for example, a silicone-based material, for allowing removal and subsequent reinsertion of the magnet. In some embodiments, the magnet holding structure may protrude away from a side of the receiver coil assembly farthest from the skin when implanted. In some embodiments, the magnet may be held within a magnet holding case.

The implantable device may also contain a signal processor module for processing at least one information signal associated with the implanted device. The magnet holding structure may include a layer of an anti-bacterial material such as a silicone material over at least a portion of an external surface of the magnet holding structure.

BRIEF DESCRIPTION OF THE DRAWINGS

FIG. 6A-D show cross-sectional views of various other embodiments of an implanted device coil assembly having an internal holding magnet contained within various differently shaped magnet cases.

FIG. 7A-B shows cross-section views of two other embodiments of an implantable device for a removable low-torque internal holding magnet case.

DETAILED DESCRIPTION OF SPECIFIC EMBODIMENTS

Embodiments of the present invention are directed to an implanted device having a low-torque internal magnet arrangement which allows for typical MRI procedures that otherwise require surgical removal and replacement of the magnet. But the magnet holding structure also is adapted to allow for easy removal and replace of the internal magnet for those MRI procedures where the magnet might produce unacceptable imaging artifacts if left in place; for example, for MRI's of the tissue in the near vicinity of the implanted device.

More specifically, embodiments are directed to an implantable device having a receiver coil assembly including a magnet holding structure for containing at least one internal holding magnet. The internal holding magnet is reorientable in responsive alignment to a direction of an external magnetic field, as for example, during an MRI examination. And the magnet holding structure is adapted for allowing removal and subsequent reinsertion of the internal holding magnet, for example, to allow for MRI imaging. For example, the magnet holding structure may use a resilient material such as a silicone material to be temporarily deformable to allow for removal and reinsertion.

Among the various considerations in specific embodiments of such an arrangement are that the surgical removal and reinsertion operations should be as unproblematic as possible. In addition, the mechanical integrity of the implanted structures should not be compromised by the surgical procedures. And the likelihood of bacterial growth should be minimized as far as possible in all parts of the implant, such as for example, along the interfaces between the various structures.

Figure 5A:
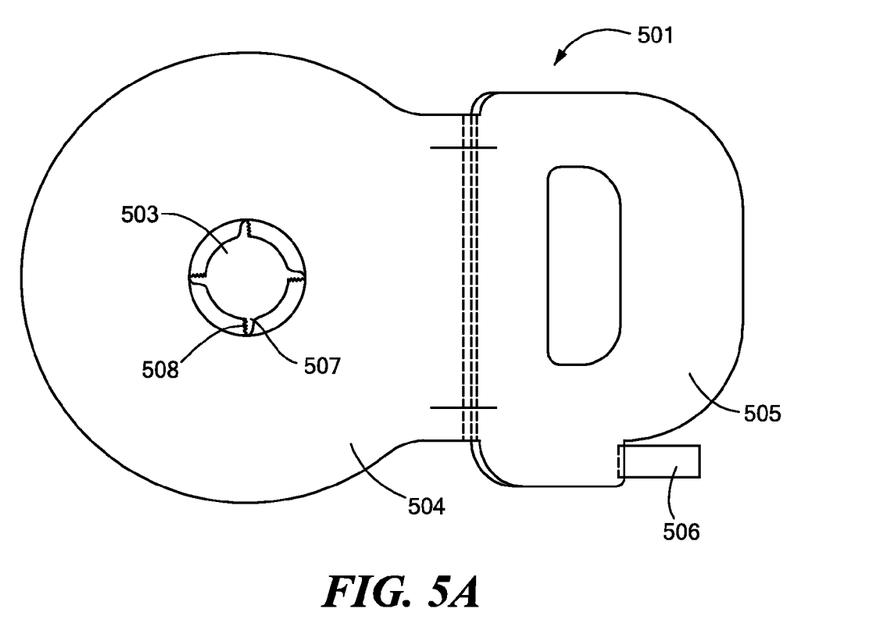
FIG. 5A shows a top plan view and FIG. 5B shows a cross-sectional view of one specific embodiment of an implanted device according to the present invention.
Figure 5B:
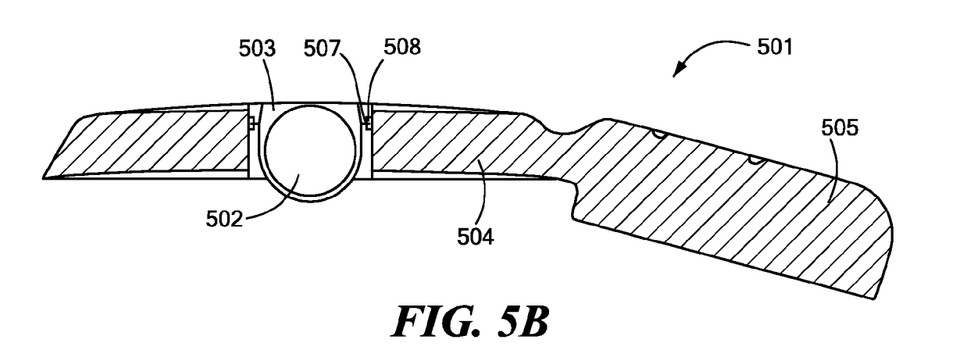

FIG. 5A shows a top plan view and FIG. 5B shows a cross-sectional view of one specific embodiment of an implanted device 501 according to the present invention. The device includes an internal holding magnet 502 and located within a spherical case magnet holding structure 503, which in the embodiment shown, protrudes away from a side of the implanted device 501 farthest from the skin when implanted. In this embodiment, it is actually the metal case magnet holding structure 503 containing the internal holding magnet 502 which is removable and replaceable.

In other specific embodiments, the internal holding magnet 502 may be cylindrical, and some embodiments may have multiple cylindrical and/or spherical internal holding magnets 502. The implanted device 501 also includes a receiving coil assembly 504 and a signal processor housing 505 which cooperate to receive an external information and/or power signal and develop an electrode stimulation signal for a processor output 506 to an implanted prosthetic electrode carrier.

The magnet holding structure 503 also includes around its circumference multiple coupling projections 507, which cooperate with corresponding coupling receptacles 508 in the receiving coil assembly 504 to hold the magnet holding structure 503 in place. The magnet holding structure 503 can be removed or replaced simply by rotating it relative to the receiving coil assembly 504. This rotation causes the coupling projections 507 and their corresponding coupling receptacles 508 to engage against each other—temporarily deforming one or both of them until they lock or unlock, depending on whether the magnet holding structure 503 is being replaced or removed.

FIG. 6A-D show cross-sectional views of various other embodiments of an implanted device coil assembly 601 having an internal holding magnet 602 contained within various differently shaped magnet cases 603. In such embodiments, all or part of the coil assembly 601 may use a resilient material to be temporarily deformable as required, for example, a bio-compatible plastic or a silicone-based material.

Figure 6A:
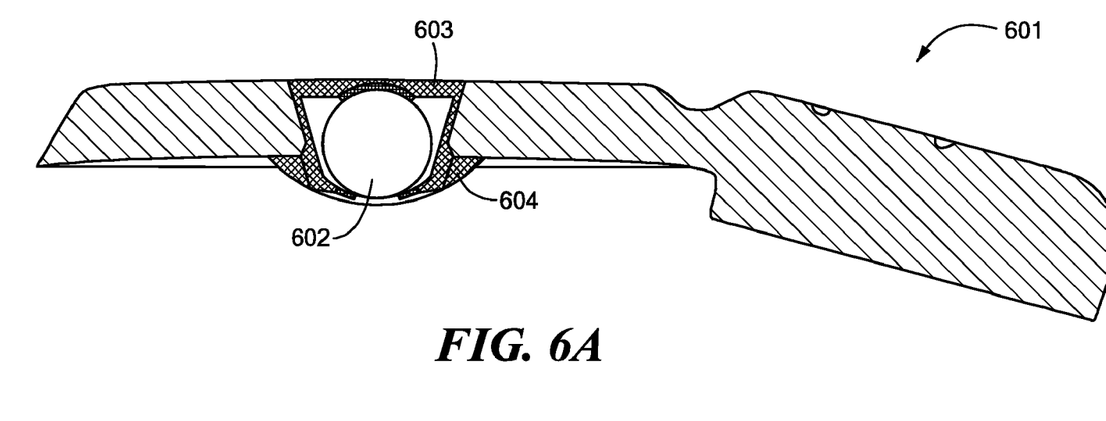
Figure 6B:
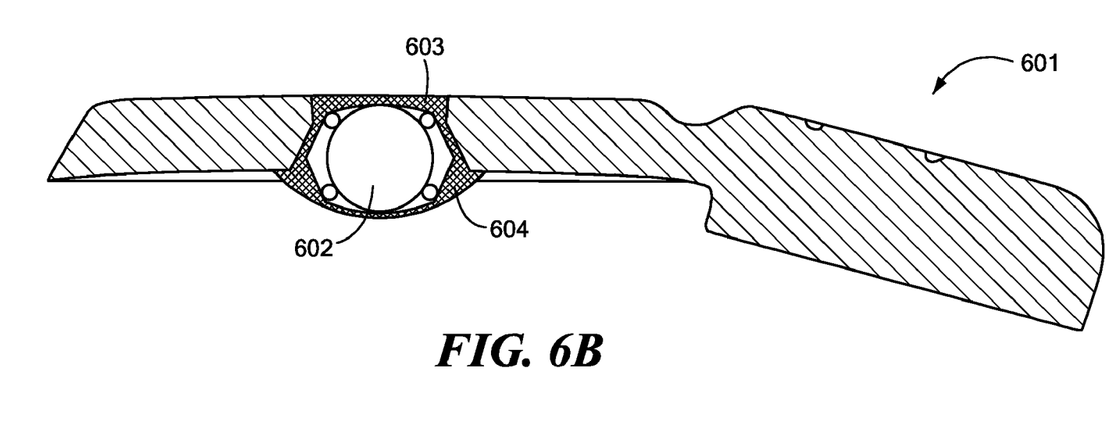
Figure 6C:
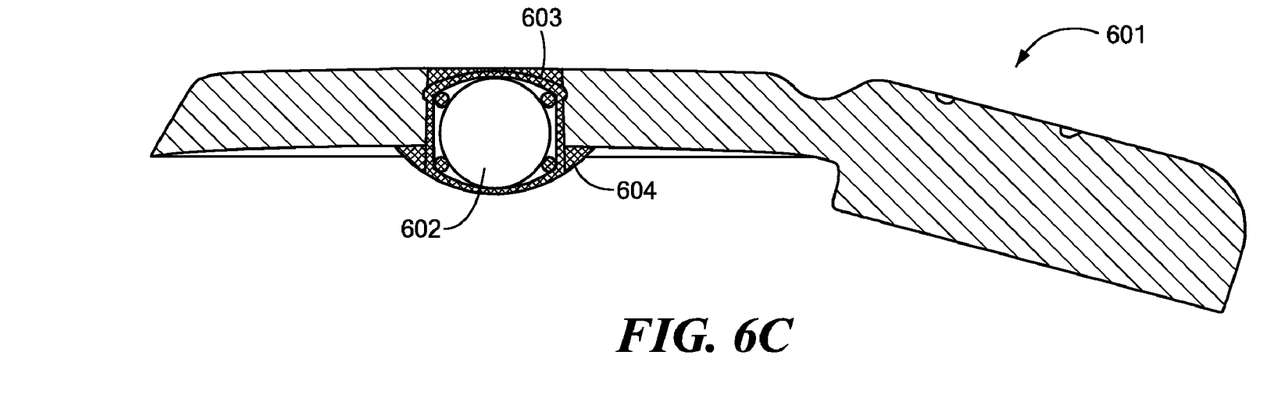
Figure 6D:
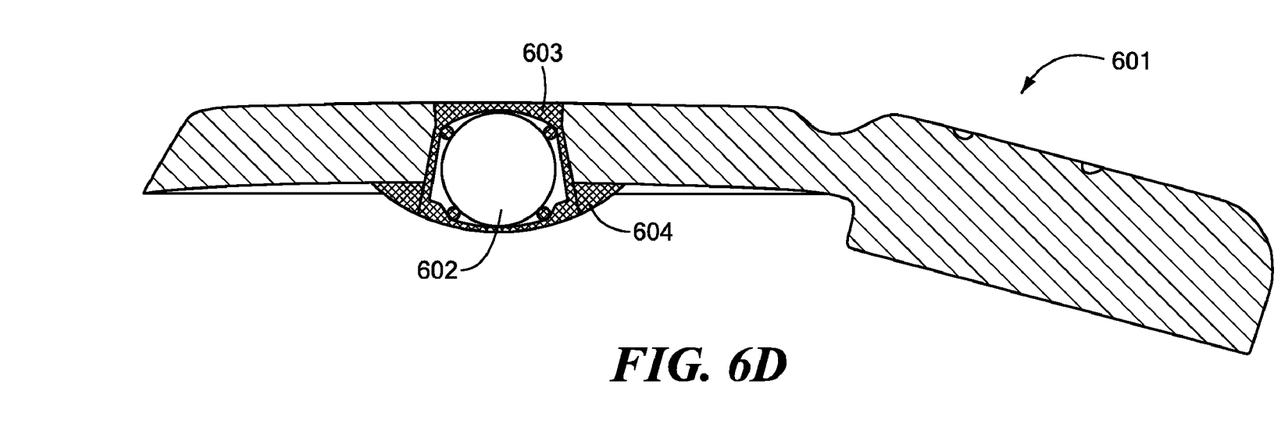

In FIG. 6A, the magnet case 603 is tapered to be wider at the top and narrower at the bottom and includes a flange head 604 as shown. Although the magnet case 603 is normally securely positioned in the implanted device 601, it can be removed simply by prying under the flange head 604. This compresses part of the coil assembly 601, temporarily deforming it so that the case 603 can slide out and separate from the implanted device 601. This can be accomplished during relatively minor surgery before MRI testing. After the MRI testing, the magnet case 603 and its internal holding magnet 602 can be replaced by a second minor surgery during which part of the coil assembly 601 is again compressed to temporarily deform it to allow it to snap back into place until the flange head 604 is resting flush against the underside of the implanted device 601. FIG. 6B-D shows different similar variations on this concept and principle.

Figure 7A:
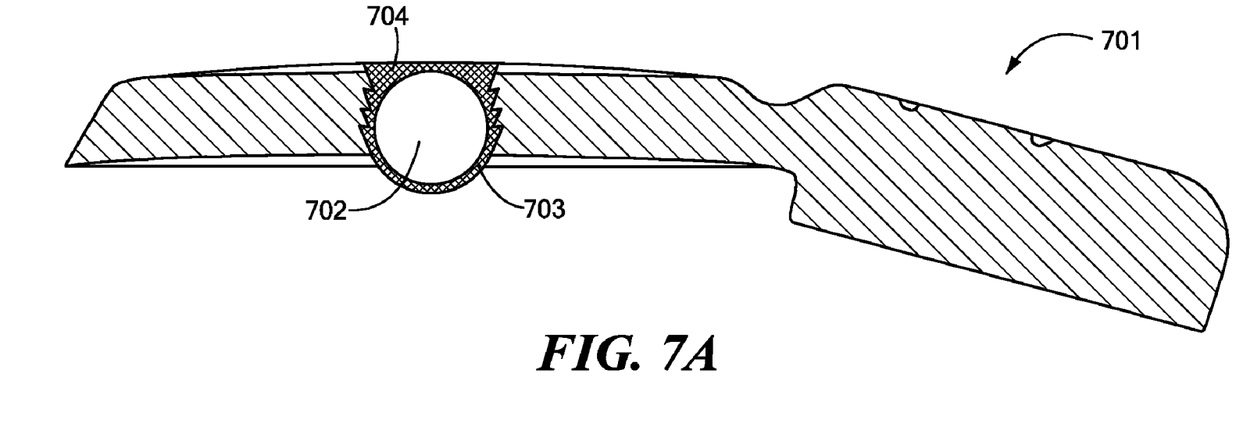
Figure 7B:
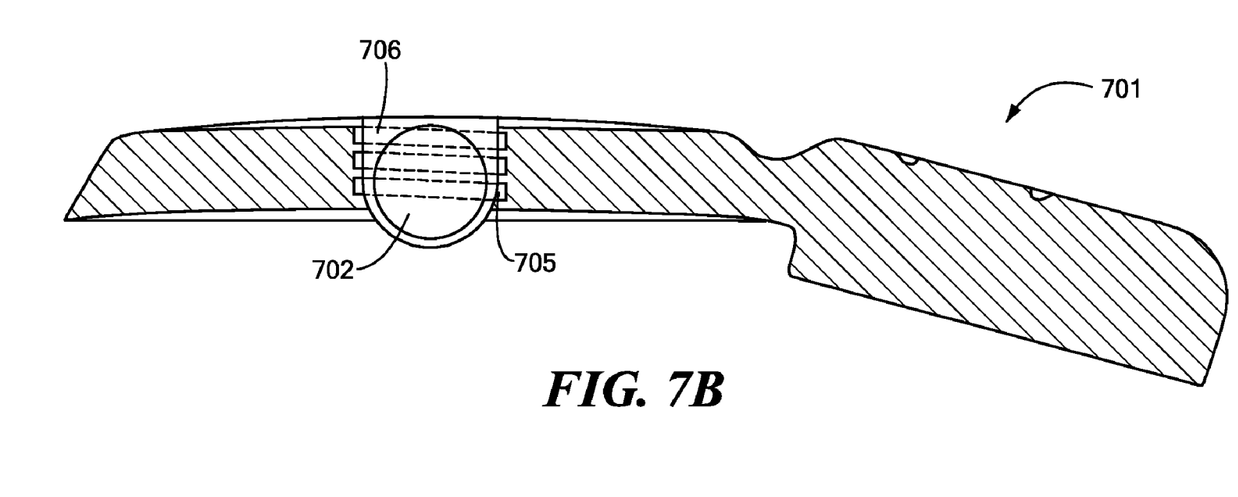

FIG. 7A-B shows cross-section views of two other embodiments of an implantable device 701 for a removable low-torque internal holding magnet case 702. In the embodiment shown in FIG. 7A, the internal holding magnet case 702 is adapted to be press-fitted into a magnet holding socket 703 which as well as the coil assembly includes tapered ribs 704. The internal holding magnet case 702 is removable from the implantable device 701 by applying force upward to deflect the tapered ribs 704 so that they temporarily deform to allow the magnet to pop up and out of the socket 703. Replacement of the internal holding magnet 702 is simply the opposite operation, pressing down on it to pop it back into the socket 703. In FIG. 7B, a coiled holding spring 706 fits into corresponding threads in the side wall of the device, thereby fixing the internal holding magnet case 702 in place. In other embodiments, the internal holding magnet case 702 itself may include threads on its exterior surface so that it can be screwed into corresponding threads in implantable device 701.

Various embodiments such as the ones described above may also be adapted so that the internal magnet holding case may be removable and/or reinsertable from the other side of the device as shown in the figures. Thus, for example, the embodiments shown in FIG. 6A-D may be adapted to be removable and/or reinsertable from the top side closest to the patient's skin. In such embodiments, the internal magnet holding case may be centered within an opening in the center of the receiving coil and covered by nearby bone, securely holding it in place. Similarly, the embodiments shown in FIG. 7A-B may be adapted to be removable and/or reinsertable from the underside farthest from the patient's skin.

Various specific embodiments may have some surfaces and/or structures coated with a therapeutic medicine such as an anti-bacterial agent to prevent or minimize bacterial growth which otherwise might be problematic, especially in the event of multiple surgeries such as the invention allows. Similarly, the interfaces between the various structural elements may be sealed, e.g. with a thin silicone layer, to prevent or minimize bacterial ingress into these interface regions. Thus, there may be a thin sealing layer between the internal magnet holding case and the coil assembly.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. An implantable device comprising:
   a spherical-shaped internal holding magnet; and
   an implantable receiver coil assembly including a magnet holding structure containing the internal holding magnet and which allows reorientation of the internal holding magnet in responsive alignment to a direction of an external magnetic field,
   wherein the magnet holding structure is adapted to allow removal and subsequent reinsertion of the internal holding magnet from the implantable receiver coil assembly while the implantable coil assembly is implanted in a patient.

2. An implantable device according to claim 1, wherein the magnet holding structure is temporarily deformable to allow removal and subsequent reinsertion of the internal holding magnet.

3. An implantable device according to claim 2, wherein the magnet holding structure is based on a resilient material.

4. An implantable device according to claim 3, wherein the resilient material is a silicone-based material.

5. An implantable device according to claim 1, further comprising:
   a hermetic case for containing the internal holding magnet, wherein the magnet holding structure is adapted to allow removal and subsequent reinsertion of the hermetic case containing the internal holding magnet.

6. An implantable device according to claim 1, wherein the magnet holding structure protrudes away from a side of the receiver coil assembly farthest from the skin when implanted.

7. An implantable device according to claim 1, further comprising:
   a signal processor module for processing at least one information signal associated with the implanted device.

8. An implantable device according to claim 1, wherein the magnet holding structure includes a layer of an anti-bacterial material over at least a portion of an external surface of the magnet holding structure.

9. An implantable device according to claim 1, wherein the anti-bacterial material includes a layer of silicone material.

\* \* \* \* \*